United States Patent [19]

Dornhagen et al.

[11] Patent Number: 5,037,511
[45] Date of Patent: Aug. 6, 1991

[54] PROCESS FOR THE PRODUCTION OF PURE DIMETHYLETHER

[76] Inventors: Horst Dornhagen, Auf dem Radacker 21, D-5047 Wesseling; Hartmut Hammer, Leyboldstr. 21, D-5000 Koln; Ewald Meisenburg, Hohenring 60, D-5357 Heimerzheim; Horst Schmid, Am Schmettenstuck 29, D-5047 Wesseling, all of Fed. Rep. of Germany

[21] Appl. No.: 344,989

[22] Filed: Apr. 28, 1989

[30] Foreign Application Priority Data

May 4, 1988 [EP] European Pat. Off. ........ 88107118.7

[51] Int. Cl.⁵ .......................... B01D 3/14; C07C 41/42
[52] U.S. Cl. ....................................... 203/37; 203/42; 203/93; 203/94; 203/96; 203/97; 203/98; 203/99; 203/DIG. 9; 203/DIG. 19; 568/698; 568/699
[58] Field of Search ..................... 203/37, 99, DIG. 9, 203/DIG. 23, DIG. 19, 42, 93, 94, 96, 97, 98; 568/698, 699

[56] References Cited

U.S. PATENT DOCUMENTS

| | | |
|---|---|---|
| 3,356,590 | 12/1967 | Johnson ........................ 203/DIG. 9 |
| 3,847,756 | 11/1974 | Statman et al. ........................ 203/96 |
| 4,560,807 | 12/1985 | Murai et al. ................. 203/DIG. 19 |
| 4,722,769 | 2/1988 | Chan et al. ............................. 203/37 |
| 4,802,956 | 2/1989 | Dornhagen et al. ................... 203/80 |

FOREIGN PATENT DOCUMENTS

| | | |
|---|---|---|
| 0099676 | 2/1984 | European Pat. Off. . |
| 0124078 | 11/1984 | European Pat. Off. . |
| 0270852 | 6/1988 | European Pat. Off. . |
| 680328 | 8/1939 | Fed. Rep. of Germany . |
| 2362944 | 7/1974 | Fed. Rep. of Germany . |
| 2757788 | 6/1978 | Fed. Rep. of Germany . |
| 2818831 | 11/1978 | Fed. Rep. of Germany . |
| 3201155 | 10/1982 | Fed. Rep. of Germany . |
| 3220547 | 1/1983 | Fed. Rep. of Germany . |
| 701335 | 3/1931 | France . |
| 332756 | 7/1930 | United Kingdom . |
| 350010 | 6/1931 | United Kingdom . |
| 403402 | 11/1933 | United Kingdom . |

OTHER PUBLICATIONS

Matthew Van Winkle, "Distillation", McGraw Hill Book Co., New York, p. 498.
"DME 99,99: High Quality, High Purity", RWE-DEA Aktiengesellshaft für Mineraloel und Chemie.

Primary Examiner—Virginia Manoharan
Attorney, Agent, or Firm—Connolly and Hutz

[57] ABSTRACT

A process for the production of pure dimethylether by feeding the dehydration product from a dimethylether-synthesis reactor into a distillation column for the production of pure dimethylether at defined trays of this column and withdrawal of pure dimethylether and a fraction containing contaminations at defined trays of the same column, whereby in addition washing liquids and bases can be added.

15 Claims, 2 Drawing Sheets

PROCESS FOR THE PRODUCTION OF PURE DIMETHYLETHER

BACKGROUND OF THE INVENTION

Up to the development of low pressure methanol synthesis processes dimethylether has been obtained in a quantity of 2 –5 weight-% as a side-product in high-pressure methanol production units and has been isolated by distillation from methanol-fractions, which contained additional low boiling side-products.

After introduction of low pressure methanol processes, which yield only negligible quantities of dimethylether, special synthetic processes have been developed, based on the catalytic dehydration of methanol. Numerous processes have been disclosed in the patent literature. For example, according to DE-PS 680 328, aliphatic ethers are obtained by heating alcohols in the presence of zinc chloride.

Other suitable catalysts for the production of ethers from alcohols are according to GB-PS 332 756, GB-PS 350 010, GB-PS 403 402, US-PS 1 873 537 and FR-PS 701 335, ferrous and ferric chloride, copper sulfate, stannic and stannous chloride, manganese chloride, aluminium chloride and -sulfate, chromic sulfate, alum, thorium compounds, aluminium oxide, titanium oxide, barium oxide, silica or aluminium phosphate.

In "Industrial and Engineering Chemistry", Vol. 41, No. 12, page 2928 (1949) use of bauxite with a $SiO_2$ portion of 4,40 –13,99 weight-% is described. In US-PS 3 036 134 an aluminium silicate-catalyst is disclosed for the production of dimethylether from methanol, with a ratio of $Al_2O_3$:$SiO_2$ of 1 part: 1,35–0,3 parts. The synthesis gas ($CO + H_2$) has also been described (DE-PS 23 62 944, DE-PS 27 57 788 and DE-PS 32 20 547).

The technically most important catalysts have turned out to be according to DE-PS 28 18 831, DE-OS 32 01 155, EP-A 0 099 676 and EP-A 0 124 078 in particular aluminium oxide and aluminium silicate catalysts with and without doping. In DE-PS 28 18 831 a catalyst for the production of dimethylether is disclosed, which can contain any aluminium oxide as a base material, as far as it possesses a sufficiently large surface and additives of 1 to 30 weight-% of rare earthes.

In EP-A 0 099 676 a catalyst is disclosed, which contains 1–20 weight-% of $SiO_2$, preferably 1–10 weight-% of $SiO_2$ and more preferably 6 weight-% of $SiO_2$.

Crude dimethylether thus obtained contains reaction water, unreacted methanol as well as small quantities of contamination, like methyl formate, hydrocarbons, aminesand sulfides, carboxylic acids and esters, amides, acetales and others.

In EP-A 0 270 852 a process is described, according to which dimethylether is produced from methanol in the presence of a catalyst, which contains very small quantities of $SiO_2$.

In synthesis units for the production of DME, crude dimethylether is worked up in two distillation columns connected in series. In the first column, which operates under pressure, pure dimethylether is obtained. In the second one unreacted methanol is distilled off. Thus in EP-A 0 124 078 a process is described, according to which dimethylether is drawn off as a sidestream in a first column, which is operated under pressure, whereas in a second column, which is operated under lower pressure, contaminations with boiling points between dimethylether and methanol, are drawn off overhead. Methanol is obtained in the same column as a side-stream. Catalysts are $Al_2O_3$, $SiO_2$, aluminum silicates and preferably $\delta$-$Al_2O_3$.

Although by this process dimethylether of higher purity compared to the state of the art is obtained, it has, from an economical point of view, a considerable disadvantage, because not only the first column, but also the second one have to be equipped with a high number of trays. This leads to high investment costs and in particular to high costs of operation. Furthermore, there exists a considerable risk, that the contaminations, boiling between dimethylether and methanol, are not completely transferred to the second column, but accumulate in the first column and are drawn off with dimethylether As a consequence a dimethylether quality is obtained, which is not free of odor.

In EP-A 0 270 852, already mentioned above, a purification process for the production of highly pure, odorless dimethylether by distillation is disclosed, characterized by withdrawal of a fraction, which contains contaminations boiling between dimethylether and methanol, in the same column from which pure dimethylether is distilled off. This fraction has to be withdrawn at defined trays as a side-stream.

Since dimethylether gains increasing importance as a propellant for sprays, very high demands are made with regard to purity. Thus, no irritating substances in dimethylether are permitted in applications like cosmetic, human and household sprays. Furthermore dimethylether has to be free of odor for these applications.

Object of the instant invention therefore was the production of a highly pure odorless dimethylether, which is also obtained by a more economical process compared to the state of the art and to convert methanol nearly quantitatively into a highly pure product which is suitable for the above named applications.

SUMMARY OF THE INVENTION

Applicant has succeeded in solving the problems outlined above by the instant inventive process.

According to the invention highly pure dimethylether is produced by catalytic dehydration of methanol at a temperature of 140°–500° C. and a pressure of 1–50 bar and distillative work-up of the dehydration product, whereby the dehydration product is fed in the gaseous and/or liquid state into a column for the production of pure dimethylether, at one or several trays and at least one tray, preferably at least 5 trays and particularly preferable at least 10 trays above the bottom of the column, characterized in that a, (a) liquid and/or gaseous fraction(s), containing contaminations are withdrawn at one or several trays, whereby the fraction(s), which contain the contaminations is (are) withdrawn at least 3 and preferably 5 trays below the lowest tray, from which pure dimethylether is withdrawn to at least 5 trays, preferably 10 trays above the bottom of the distillation column;

b, the tray and in the case of several trays the lowest tray, from which pure dimethylether is withdrawn, is in the case of one feed tray at least 8 trays, preferable at least 10 trays and particularly preferable at least 12 trays above the feed tray; and in the case of several feed trays, if the quantity of dehydration product, which is fed to the highest feed tray is >0–<100% of the total feed, the lowest tray from which pure dimethylether is withdrawn is a least one to at least 8 trays above the highest feed tray, whereby the distance of trays increases with increasing quantity of feed, fed to the highest feed tray.

DETAILED DESCRIPTION OF THE INVENTION

According to the state of the art, the determination of substances with an unpleasant odor is carried out predominantly by empirical methods, in particular by sensory determination by a trained team. Thus, the limit of inconvenience in case of $H_2S$ has for example been identified in the Federal Republic of Germany by 150 persons as 45 $\mu g/m^3$. (Schriftenreihe der Landesanstalt für Immissionsschutz des Landes Nordrhein-Westfalen, Heft 49 (1979), page 77). In those cases, where the limit of perception of odor can be analyzed by instruments, gaschromatography, electric conductivity, photometry or fluorescence measurement are applied ("Erdöl und Kohle-Erdgas-Petrochemie," Vol. 32, Nr. 2, Febr. 1975, page 86). The determination of odor in the instant application is based on the sensory method. Crude methanol from methanol synthesis units as well as dimethylether produced catalytically from methanol, contain as outlined above, numerous contaminations, with, in some cases, strong odor. Whereas from high-pressure-methanol synthesis units crude methanol is obtained, which in general contains 2-3, however up to 5 weight-% of dimethylether, crude dimethylether which is produced from crude or pure methanol in dimethylether synthesis units, consists in general of 20 to 80 weight-% of dimethylether and in addition of the above named contaminations, reaction water and unconverted methanol. Since the boiling points of the contaminations, for example of methyl amine (b.p. $-7,55°$ C./719), of dimethyl amine (b.p. $6,9°$ C.), trimethyl amine (b.p. $-3°$ C.), dimethyl sulfide (b.p. $37,3°$ C.), methyl mercaptane (b.p. $5,8°$ C.), formic acid (b.p. $100,75°$ C.), formic acid methylester (b.p. $31,5°$ C.), formaldehyde (b.p. $-21°$ C.), formaldehyde dimethyl acetale (b.p. $45,5°$ C.) or acetic acid methylester (b.p. $56,95°$ C.), as well as solubilities and vapor pressures are very different and since the intensity of odor of the individual compounds is also very different and in addition numerous azeotropic mixtures are formed, the object of obtaining highly pure, odorless dimethylether in high yield by a particularly economical process is very difficult to achieve.

The investigations of applicant, which have been carried out during several years in numerous test sequences, in laboratory, pilot plant and technical unit, have non-obviously led to the result that highly pure, odorless dimethylether can be produced nearly quantitatively, based on the dehydration product obtained from the dimethylether synthesis reactor in an particularly economical way by the inventive distillative purification.

A particularly suitable catalyst for the instant invention are catalysts of the $\delta\text{-}Al_2O_3$-type disclosed by applicant in EP-A 0 270 852. Unlike the catalysts of the state of the art, they contain only very small quantities of $SiO_2$ and lead to considerably better results than the known catalysts. The preferred $SiO_2$-concentration is $>0$ to $<1$ weight-%, a preferred concentration is 0,001 to 0,5 and a particularly preferred concentration is 0,001 to 0,2 weight-% $SiO_2$.

The inventive process can be operated discontinuously however preferably continuously.

The investigations of applicant have led to the result, that in order to obtain highly pure, odorless dimethylether by a particularly economical process in nearly quantitative yield, crude product from the reactor has to be fed to the distillation column for the production of pure dimethylether at one or several trays at least one tray, preferably 5 trays and particularly 10 trays above the bottom of the dimethylether distillation column.

Furthermore, according to the invention, pure dimethylether is withdrawn in the case of one feed tray at least 8 trays, preferably at least 10 trays and particularly preferable 12 trays above the feed tray and in the case of several feed trays if the quantity of dehydration product, which is fed to the highest feed tray is $>0-<100\%$ of the total feed, the lowest tray from which pure dimethylether is withdrawn is a least one to at least 8 trays above the highest feed tray, whereby the distance of trays increases with increasing quantity of feed, fed to the highest feed tray.

Preferred trays for withdrawing pure dimethylether are the 15th and higher trays (closer to the head of the column). It is also possible to withdraw pure dimethylether at the head of the column. As mentioned above, withdrawal of pure dimethylether can also take place at several trays. Pure dimethylether can be withdrawn in a liquid and/or gaseous state. Furthermore the investigations of applicant have led to the result that (a) fraction(s) containing contaminations is (are) withdrawn in a liquid and/or gaseous state in the same column at one or several trays, whereby the fraction(s) containing contaminations is (are) withdrawn at least 1, preferably at least 3 and particularly preferable at least 5 trays below the lowest tray for withdrawal of pure dimethylether to at least 5 trays, preferably at least 10 trays above the bottom of the column.

According to the invention it is possible to withdraw fractions, which contain contaminations in a gaseous and/or liquid state at one or several trays in the part of the column described above, whereby as outlined already, the quantity of dimethylether increases in these fractions, as more closely the tray for withdrawal of contaminations is located to the tray(s) for withdrawal of pure dimethylether.

Accordingly the contaminations are withdrawn in a distance of at least 3, preferably of at least 5 trays below the tray for withdrawal of dimethylether and in the case of several trays below the lowest tray for withdrawal of dimethylether.

More general, product which contains contaminations can be withdrawn beginning with the 5th tray, preferably with the 10th tray from the bottom to the third tray below the dimethylether tray in a gaseous and/or liquid state.

According to the invention, the quantity of the fraction, which contains contaminations can be varied in broad limits, thus in the case of a sufficient quantity a product can be obtained, which can be used as technical dimethylether, which can be used for example for the production of dimethyl sulfate or for the use in sprays, where lack of odor is not requested. Transformation of this DME-quality into gasoline is also possible. Technical grade dimethylether is of course a less pure dimethylether, which is not free of odor. In general the tray from which a fraction, containing contaminations, is withdrawn, may be as closer to the tray from which pure dimethylether is withdrawn, as larger the quantity of distillate is desired to be.

According to the invention, in addition to the dehydration product, a washing liquid may be added, preferably methanol. This may be pure methanol, crude methanol are other grades of methanol. Crude methanol is methanol directly obtained from the methanol synthesis reactor, and may originate from a low pressure, medium pressure or high pressure synthesis, whereas pure methanol is a grade purified by distillation, characterized by national and international specifications. A different methanol grade may be obtained by distilling off light components like $CH_4$, $CO_2$, $N_2$ and other components for example in a first runnings distillation column. However the washing liquid may also be water or a methanol/water mixture or dimethylether itself or as a blend with water and/or methanol. The washing liquid may be added to the dehydration product, before the latter is introduced into the distillation column. As a consequence the mixture of dehydration product and washing liquid enters the feed tray(s).

Basically the dehydration product may at least in part together with or without washing liquid be introduced into the distillation column in the gaseous state.

Alternatively a mode of operation may be selected, whereby the washing liquid is fed to the same tray(s) separately or at least in part separately, the dehydration product is fed to.

A further inventive mode of operation is the addition of washing liquids to other trays than the dehydration product. Preferably the washing liquid is fed to a feed tray or to a tray below the lowest feed tray.

According to the invention it is also possible, to wash at least part of the dehydration product in a washing device located in front of the distillation column. Whereas the washed, gaseous dehydration product flows to the distillation column, the washing liquid, which contains the contaminations may be fed separately to the lower part of the distillation column.

Addition of a washing liquid has the favorable result of an additional purification effect with regard to pure dimethylether to be produced. The quantity of added washing liquid may vary in broad limits from >0% based on the quantity of dehydration product feed up to a quantity several times as much as the dehydration product feed. Decisive is the desired quality of the pure dimethylether.

In case that contaminations, respectively an odor is detected in the dimethylether, for example as a result of low quality of methanol used in the dimethylether synthesis, the quantity of added washing liquid should be varied.

A further criterion regarding the quantity of washing liquid is the quantity of crude methanol produced in a methanol synthesis unit in the case that the dimethylether distillation is integrated into a crude methanol distillation unit.

In such a case the ratio of quantity of crude methanol to dehydration product may vary strongly, depending on the production capacity of the methanol synthesis unit and the dimethylether synthesis unit, if both products are distilled together in the same distillation unit and the pure dimethylether is produced in this unit according to the instant invention.

This becomes obvious to the artisan, if one considers that methanol synthesis units have an annual capacity of 100.000 –600.000 tons, whereas annual production capacities of dimethylether synthesis units are 5.000–100.000 t/a. For example in the case of a dimethylether unit of a capacity of 5.000 t/a and a methanol capacity of 500.000 t/a the ratio of dehydration product to methanol is 1:100. On the other hand the quantity of the washing liquid may be only a fraction of the quantity of dehydration product, for example 1/100, 1/20, 1/10 or 1/5. The same applies to the use of other washing liquids than methanol.

Furthermore it may be of advantage, to adjust a defined pH of at least 7 in the bottom of the dimethylether distillation column, in particular if crude methanol is present. Preferable the pH is adjusted to >7 and particularly preferable to >8 by addition of a base, in particular of NaOH, KOH and other alkali or alkaline earth bases or their mixtures.

Basically the base can be added at any position within or outside of the dimethylether column, preferably at the tray below the tray, where the distillate is withdrawn, which contains contaminations.

According to the invention the base may also be added to the pipe for dehydration product or the mixture of dehydration product and methanol, respectively washing liquid in front of the distillation column. This leads to blending of both compounds already within the pipe. The base may also be added together with the washing liquid.

The modes of addition of the base respectively base mixtures discussed, are to be considered as examples, not however as limiting.

Base may be added alternatively already in a first runnings distillation column if available.

The reflux ratio in the dimethylether column can be varied depending on the concentration of dimethylether in the dehydration product.

The extensive investigations of applicant have led to the non-obvious result, that in the case of only one feed tray, a highly pure dimethylether free of odor is obtained, if the lowest tray from which pure dimethylether is withdrawn is at least 8 trays higher, preferably 10 trays and particularly preferable 12 trays above the feed tray for the dehydration product, for example, if the feed tray is the 26th (from the head of the column), pure dimethylether can be withdrawn already at the 18th tray or any higher tray. The distillate containing the contaminations can than be withdrawn at the 15th tray (from the head of the column) or a lower tray down to the 5th tray above the bottom.

Preferably the fraction containing the contaminations should be withdrawn at least 10 trays above the bottom and at least 5 trays below the tray for the withdrawal of pure dimethylether.

In the case of several feed trays, if the quantity of dehydration product, which is fed to the highest feed tray is >0–<100% of the total feed, the lowest tray from which pure dimethylether is withdrawn is a least one to at least 8 trays above the highest feed tray, whereby the distance of trays increases with increasing quantity of feed, fed to the highest feed tray.

The investigations of applicant furthermore have led to the non-obvious result that the adjustment of the pH in the bottom of the dimethylether column is of great influence on the odorous components in dimethylether.

Thus even within the scope as stated in claim 1, their may be borderline cases at certain modes of operation, where odorous components appear in pure dimethylether, for example if the reflux ratio is very low at an only small concentration of dimethylether in the feed to the column (since within the claimed scope the reflux ratio has to be chosen in such a way that the desired pure dimethylether is obtained). In another case odorous components may be present in pure dimethylether, if only a very small fraction containing contaminations is withdrawn whereas dimethylether is withdrawn in nearly quantitative yield (according to the invention such a quantity of distillate containing contaminations has to be withdrawn, that the odorous components are quantitatively or nearly quantitative included in this fraction. This quantity can be easily determined by taking samples after start-up of the column and sensory analysis of the samples).

Furthermore methanol, which contains a relatively large quantity of odorous contaminations, which is fed to the dimethylether synthesis, can lead to odor problems or recycling of methanol, which has been distilled off in the methanol column following the dimethylether column, depending on the contaminations in the recycle methanol.

By adjustment of the pH according to the invention in the bottom of the dimethylether column also in these cases an excellent odorfree dimethylether can be obtained. A pH>8 is preferred, particularly of 8-12, but other pH-adjustments to at least 7 and higher lead to the inventive result.

With regard to the reflux ratio, a ratio of 1:0,2 to 1:100, preferably of 1:0,2 to 1:25 is chosen in the case of a feed product to the dimethylether column (washing liquid included, if used), which contains >0-5 weight-% of dimethylether.

If the dimethylether concentration in the total feed is 20 -80 weight-%, the ratio to be chosen is 1:0,2 to 1:50, preferably of 1:1 to 1:5.

If the dimethylether concentration is >5 to <20 weight-% of dimethylether, the reflux ratio to be chosen is 1:0,2 to 1:50, preferably of 1:0,2 to 1:25 and if the dimethylether concentration is >80 to <100 weight-%, a reflux ratio of 1:0,2 to 1:10 is preferred and of 1:0,2 to 1:5 particularly preferred, whereby a decreasing reflux ratio is selected with increasing dimethylether concentration in the feed.

A reflux ratio of for example 1:1 means that the quantity of dimethylether withdrawn is 1 part and the quantity of vapor condensed at the head of the column is 1+1 parts (the first number represents the quantity withdrawn).

A reflux ratio of 1:5-8 is for example suitable for a feed product with a dimethylether concentration of 3-4 weight-%. This is a typical concentration in crude methanol as obtained in high-pressure methanol synthesis. Basically dimethylether can only then be obtained in a highly pure, nearly quantitative yield, if the inventive positions of feed tray(s) and trays for withdrawal of dimethylether and distillate containing contaminations are selected.

If the feed product contains for example 20-80 weight-% of dimethylether, as well as methanol, contaminations and optionally water and other oxygen containing components, like for example alcohols with a number of C-atoms >1, a reflux ratio should be chosen of 1:0,2 to 1:50, preferable of 1:0,5 to 1:10 and particularly preferable of 1:1 to 1:5 depending on the dimethylether concentration. For example in case of a blend containing 60 weight-% of dimethylether and 15 weight-% of methanol besides water and contaminations, a reflux ratio may be adjusted of 1:1 to 1:25.

These dehydration products are typical mixtures, obtained as straight run products in the catalytic production of dimethylether from methanol with Alhd $2O_3$-respectively $Al_2O_3/SiO_2$-catalysts.

The reflux ratios specified above are not to be considered as limiting. Depending on the concentration of dimethylether in the dehydration product, respectively feed, to be distilled, the artisan can select the appropriate reflux ratio within the scope of the claims. In general a decreasing dimethylether concentration necessitates an increasing reflux ratio.

The distillation column for the production of pure dimethylether is generally operated at a pressure of 5-10 bar, whereby the pressure is preferably adapted to the preceeding synthesis rector. However pressure below or above 5-10 bar can also be applied according to the invention, in particular higher pressures. The throughput is determined as usual by column design, heat supply and reflux ratio.

In order to obtain pure dimethylether nearly quantitatively, in particular in case of small concentrations in the feed product, waste gas, which leaves the column at the top and which contains small quantities of dimethylether mixed essentially with $CO_2$, $N_2$ and hydrocarbons, is washed in a washing device. The washing liquid can be recycled to the distillation column or to the synthesis reactor.

Suitable washing liquids are for example methanol or bottoms of the dimethylether distillation column.

The washing process can be operated in parallel flow, counter-currently, or crossflow, preferably countercurrently. The distillate, which is withdrawn as a sidestream and which contains the contaminations can be stripped in a side-stripper. The stripping product, containing small quantities of dimethylether, can be recycled to the column. p Methanol can be separated from water in a column, which succeeds the dimethylether column.

According to the invention, distillation columns of the state of the art can be used with the capacity desired.

Trays can be those of the state of the art, for example valve trays, sieve trays, bubble trays and other trays of the state of the art. In principle also packed columns can be used, which are equipped for example with ceramic, metal or plastic materials, glass materials, wire mesh and other materials of the state of the art. In case of packed columns the inventive locations for introducing the feed and withdrawal of dimethylether and distillates containing contaminations, can be calculated based on the required number of trays according to the invention.

BRIEF DESCRIPTION OF THE DRAWINGS

The invention is described in more detail with the aid of examples disclosed in FIGS. 1 to 4.

Figure 1:
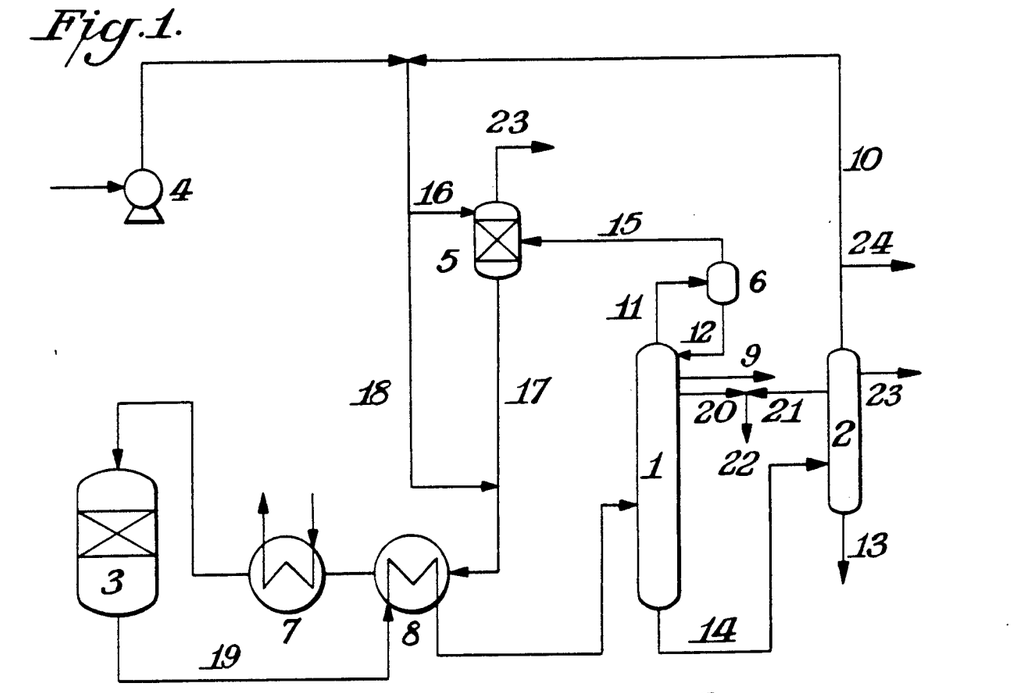
FIG. 1 represents exemplarily a unit for the production and purification of dimethylether.

In FIG. 1 (3) represents the dehydration (synthesis) reactor. Fresh methanol is fed to the reactor through pump (4), pipe (18) and heat exchangers (8) and (7).

(1) is the distillation column for the production of pure dimethylether. The column usually is operated at a pressure, which is related to the synthesis reactor, in general at a lower pressure. If for example, the synthesis pressure is 8-12 bar, the column can advantageously be operated for example at 6-11,5 bar.

These data are however not to be considered as limiting. In general it is preferred to operate reactor and distillation column at a pressure difference of 0 to 10 bar.

Highly pure dimethylether is withdrawn at (9). Head vapors are fed through (11) to condenser (6). Reflux is recycled through (12) to column (1).

Waste gas is introduced through (15) into washing device (5), where it is washed with methanol (16). In principle other washing liquids can also be used like for example crude methanol or bottoms of column (1). In the latter case the washing liquid, which contains dimethylether is recycled to column (1). Small quantities of dimethylether are fed to reactor (3) through (17), mixed with washing methanol. Waste gas is withdrawn at (23). Synthesis product (19) is fed to (1) through heat exchanger (8). At (20), contaminations boiling between methanol and dimethylether are withdrawn and can be incinerated for example. Bottoms of (1), essentially containing methanol and water are fed to column (2) through (14).

The methanol column usually is operated at normal pressure, however it may also be operated at higher or lower pressure. In general the pressure is lower than in column (1). Methanol is withdrawn through (10) and recycled to the synthesis reactor. From the bottom of (2), waste water is withdrawn through (13). If necessary, contaminations with boiling points higher than the boiling point of methanol, can be withdrawn at (21). Methanol can also be withdrawn as a sidestream (23). If necessary, contaminations then can be withdrawn overhead (24).

Figure 2:
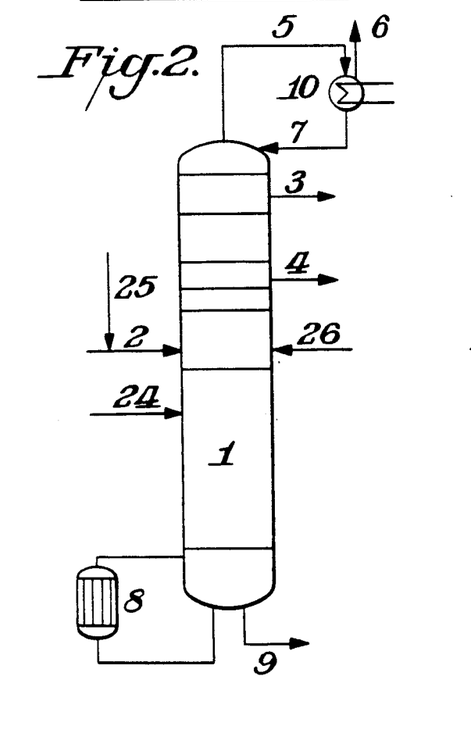
In FIG. 2 exemplarily a distillation column for the production of pure dimethylether is shown.

In FIG. 2, (1) represents the distillation column for the production of pure dimethylether. feed product is introduced at (2). Pure dimethylether is withdrawn at (3).

Contaminations are withdrawn at (4). Head vapors are fed through (5) to condenser (10). Reflux is recycled trough (7) to column (1). Waste is discharged at (6). (8) represents the reboiler cycle. At (9) bottoms are withdrawn. Washing liquid can for example be introduced through (24) and/or (25) and/or (26).

Figure 3:
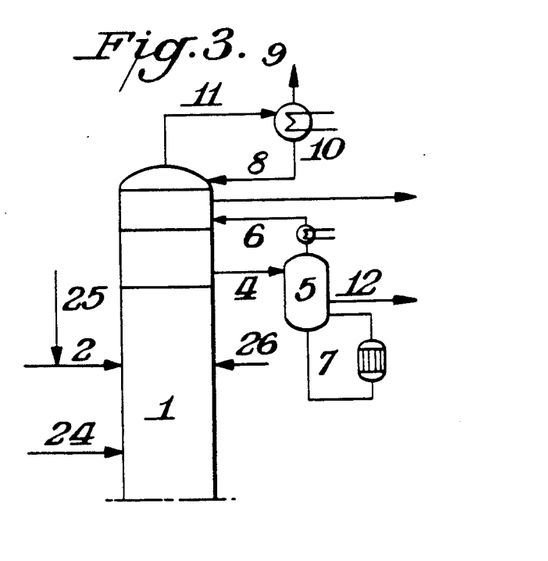
In FIG. 3 exemplarily a column is shown which is equipped with a side-stripper.

In FIG. 3 the fraction, which contains the contaminations, is passed to stripper (5) through (4). (5) is equipped with reboiler cycle (7). Stripped dimethylether is recycled to column (1) through (6). At (2) feed product is introduced. At (3) pure dimethylether is withdrawn. Head vapors pass through (11) to condenser (10). Reflux is recycled through (8) to column (1). Waste is discharged at (9). At (12) contaminations are withdrawn. Washing liquid can for example be introduced through (24) and/or (25) and/or (26).

Figure 4:
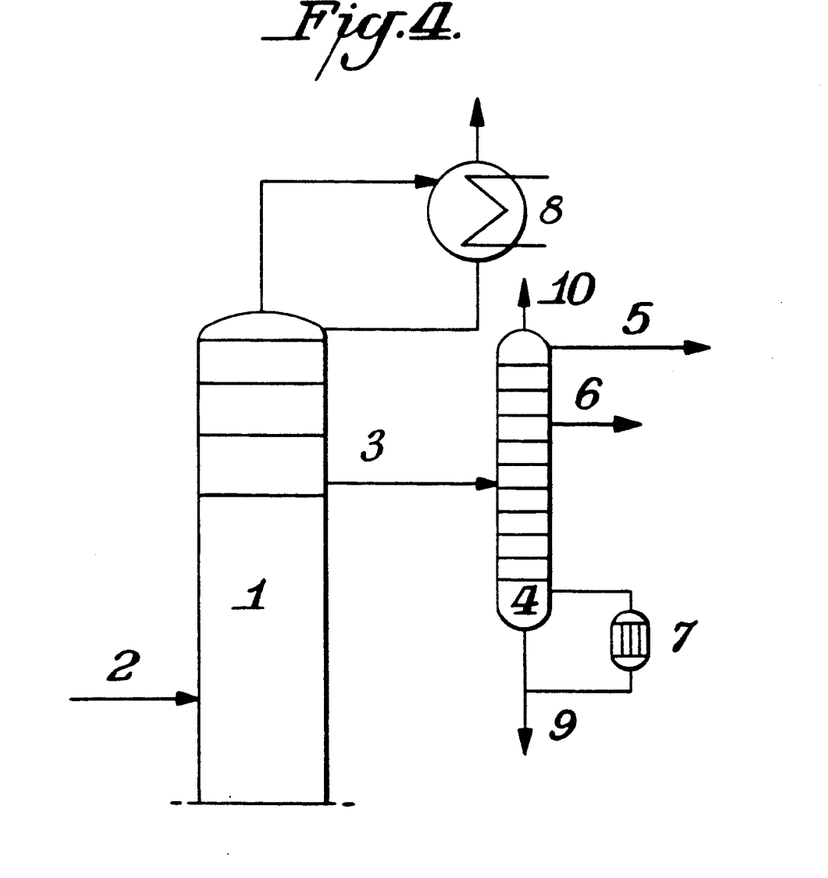
In FIG. 4 the combination of two dimethylether columns is represented.

In FIG. 4 a practically 100 % dimethylether fraction with odorous contaminations from column (1) is fed through pipe (3) to a second dimethylether column (4). In this column a pure, odorless dimethylether is withdrawn according to the invention through (5). A small quantity of distillate containing the odorous contaminations is withdrawn at (6). (7) represents the reboiler. At (9) bottoms are withdrawn and headproduct can be withdrawn at (10).

According to the instant invention highly pure dimethylether is obtained from the distillation column nearly quantitatively. Dimethylether thus obtained is free of odor, contains less than 10 ppm of methanol in general <1 ppm, a maximum of 0,1 weight-% of hydrocarbons in general <50 ppm, and is of a purity of at least 99,9 weight-% of dimethylether. Dimethyl-purity ether obtained according to the invention is excellently suited for any application in the field of aerosol sprays.

EXAMPLES

In the following examples the invention is described in more detail.

In examples 1-7 a distillate fraction containing contaminations and mainly dimethylether, which has been withdrawn from a dimethylether column in operation, was added to a dehydration product. In addition small quantities of contaminations with boiling points higher than methanol from a methanol distillation were added.

(The statement "odor" means odor caused by contaminations, but not the very slight inherent smell of dimethylether itself. Thus free of odor or odorless means that no odor caused by contaminations could be detected).

The ppm-quantities of methanol and hydrocarbons stated in the examples have not been considered in the total balance.

If not stated otherwise, the tray numbers are counted beginning at the head of the columns.

EXAMPLE 1

4493 kg/h of a dehydration product were fed to a column equipped with 65 valve trays at the 48th tray. The dehydration product consisted of 2600 kg of dimethylether (DME), 720 kg of methanol, 1060 kg of water and 113 kg of contaminations (with 90 kg dimethylether). In addition 2000 kg/h of pure methanol were fed to the column through the same pipe. The column was operated at 8 bar. The reflux ratio was 1:3. At the head of the column 5 kg/h of off-gas were withdrawn, which consisted essentially of inerts. At the 5th tray of the column 2609 kg/h of pure, odorless dimethylether were withdrawn with a methanol concentration of 1 ppm and hydrocarbon content below the detection limit (<50 ppm).

At the 37th tray 92 kg/h (with 81 kg DME) of distillate, containing contaminations were withdrawn. 12 kg/h of components boiling higher than methanol, 2720 kg/h of methanol and 1060 kg/h of water were withdrawn at the bottom and fed into a column for the distillation of methanol.

COMPARATIVE EXAMPLE 1a

Example 1 was repeated, however without additional methanol. The reflux ratio was 1:3. 6 kg/h of gas were withdrawn at the head of the column, essentially consisting of inerts. At the 5th tray 2594 kg/h of pure odorless dimethylether were withdrawn with a methanol concentration of 1 ppm and a hydrocarbon concentration below the detection limit. At the 37th tray, 107 kg/h (with 96 kg of DME) of a distillate containing contaminations were withdrawn. 12 kg/h of higher boiling contaminations, 720 kg/h of methanol and 1060 kg/h of water were withdrawn from the bottom.

EXAMPLE 2

Into the same column as in Example 1, the same feed was introduced. The column was operated as in example 1, however the contaminations were withdrawn from the 7th tray. The pure dimethylether thus obtained was nearly odorless and contained <1 ppm of methanol and hydrocarbons below the detection limit.

COMPARATIVE EXAMPLE 2a

Example 2 was repeated however without additional methanol. DME thus obtained had a clearly stronger odor compared to example 2 and contamined <1 ppm of methanol and 55 ppm of hydrocarbons.

EXAMPLE 3

66.000 kg of a dehydration product were added to a distillation column equipped with 100 valve trays. The dehydration product contained 62.000 kg of methanol, 2500 kg of dimethylether, 980 kg of water and 520 kg (with 237 kg of DME) of a distillate containing contaminations. The column was operated at 7,5 bar. The reflux ratio was 1:10. 10.000 kg/h of crude methanol were added at the 60th tray. The crude methanol originated from a Lurgi-Low pressure methanol unit and contained 93 weight-% of methanol, 0,5 weight-% of hydrocarbons+higher alcohols (0,3%) and 6,5 weight-% of water. The dehydration product was fed to the column at the 48th tray (from the head). 298 kg/h (with 209 kg DME) of a distillate containing contaminations was withdrawn at the 42nd tray. 2528 kg/h of pure dimethylether were withdrawn at the 4th tray. 11 kg/h of off-gas were withdrawn essentially consisting of inerts. 244 kg/h of higher boiling contaminations (50 kg originating from the added crude methanol), 71.300 kg/h of methanol and 1630 kg/h of water were withdrawn at the bottom. The pure DME contained 21 1 ppm of methanol and 99 ppm of hydrocarbons and was completely odorless.

COMPARATIVE EXAMPLE 3a

Example 3 was repeated, however without addition of crude methanol. The reflux ratio was 1:7. 2487 kg/h of odorless dimethylether were obtained, which contained <50 ppm of hydrocarbons and <1 ppm of methanol.

EXAMPLE 4

A mixture of 40.000 kg/h of crude methanol and 3.500 kg/h of dehydration product were fed to a column equipped with 100 bubble trays at the 46th tray. The crude methanol corresponded to the quality as stated in example 3 and was taken directly from the pressure separator of a methanol synthesis unit. The dehydration product consisted of 2.200 kg of dimethylether, 861 kg of water, 385 kg of methanol and 54 kg (with 29 kg of DME) of contaminations. The operating pressure was 6,5 bar and the reflux ratio was 2183 kg/h of pure dimethylether were withdrawn at the 6th tray of the column. 8 kg/h of off-gas were taken overhead. At the 36th tray, 55 kg/h (with 46 kg of DME) of a distillate containing contaminations were withdrawn. 3461 kg/h of water, 37.585 kg/h of methanol and 216 kg/h of higher boiling components were withdrawn. A pure, odorless DME was obtained, which contained 1 ppm of methanol and <10 ppm of hydrocarbons.

EXAMPLE 5

Example 1 was repeated, however with 20.000 kg/h of water added instead of crude methanol. A pure, odorless dimethylether was obtained with 1 ppm of methanol and <50 ppm of hydrocarbons. Similar results were obtained with methanol/water-mixtures.

EXAMPLE 6

Work-up of the dehydration product (feed 3000 kg/h with 65 weight-% of dimethylether) was carried out in 2 continuously operating distillation columns operated in series. The first column was equipped with 25 valve trays and the second one with Raschig rings (packing material). Pure dimethylether was obtained in the first column at 7 bar at the 4th tray at a reflux ratio of 1:2. The feed was added at the 12th tray. The distillate containing contaminations was withdrawn at the 14th tray. In the second column unreacted methanol was recovered. An odorless dimethylether was obtained.

COMPARATIVE EXAMPLE 6a

Work-up was carried out as in Example 6, however the contaminations were withdrawn at the head of the second column. Dimethylether thus obtained had a distinct odor caused by contaminations.

COMPARATIVE EXAMPLE 6a

Example 6a was repeated, however additionally 3000 kg/h of crude methanol were fed to the column together with the dehydration product. Dimethylether thus obtained had a slight odor.

EXAMPLE 7

As in Example 3, 65.955 kg/h of dehydration product were fed to the column, which consisted of 7.200 kg of DME, 57.230 kg of methanol, 1050 kg of water and 475 kg (with 425 kg DME) of a distillate containing contaminations. The reflux ratio was 1:0,2. The quantity of dimethylether withdrawn at the 12th tray was 7342. kg. Although a distillate of 333 kg (with 283 kg of DME) containing contaminations was withdrawn at the 18th tray, whereby 3 kg/h of off-gas were withdrawn at the head, the DME had a weak odor as a result of the low reflux ratio based on the low DME-concentration in the feed.

COMPARATIVE EXAMPLE 7a

Example 7 was repeated, however NaOH dissolved in water (12%) was added to keep the bottom at a pH of 10-11.

The DME thus obtained, was completely odorless.

EXAMPLE 8

4000 kg of dehydration product were distilled in a column equipped with 50 valve trays. The product was fed to the column at the 27th tray and contained 3120 kg of dimethylether, 420 kg (with 40 kg of DME) of a distillate containing contaminations and 414 kg of methanol. The column was operated at 8 bar and a reflux ratio of 1:25. 3150 kg of DME were withdrawn at the 15th tray. 16 kg of a distillate containing contaminations (with 10 kg of DME) were withdrawn at the 18th tray. 2 kg of off-gas consisting essentially of inerts were withdrawn at the head. A mixture of 420 kg/h of water and 414 kg/h of methanol was fed to the methanol column. As a result of withdrawal of only a small quantity of distillate containing contaminations, at a tray 3 trays below the tray where DME was withdrawn and as a result of the high yield of DME withdrawn (99,6% of the DME in the feed) at the 15th tray, the DME obtained had a weak odor.

COMPARATIVE EXAMPLE 8a

Example 8 was repeated, however aqueous KOH was added to keep the bottom at a pH of 8-9. DME thus obtained was odorless. An analogous result was obtained by addition of Ca(OH)$_2$.

In the following Examples 9-10 the feed from a DME-synthesis reactor was fed continuously to the distillation column. The time of operation was 720 hours for each trial.

EXAMPLE 9

The product from the DME-synthesis reactor consisted of 1046 kg of methanol, 1442 kg of water and 3773 kg of dimethylether. This mixture was fed to the distillation column with a temperature of 112° C. at the 53rd tray. The column was equipped with 61 valve trays and was operated at a reflux ratio of 1:3. 60 kg/h (with 57 kg of DME) of distillate, containing contaminations, were withdrawn at the 50th tray. 3716 kg/h of pure DME were withdrawn at the 45th tray. 3 kg of off-gas, essentially consisting of inerts, were withdrawn at the head of the column. The bottoms of 2486 kg/h were fed into the methanol column equipped with 40 valve trays and separated into 1044 kg of methanol, withdrawn overhead and 1442 kg of water withdrawn at the bottom. The DME thus obtained was odorless and contained 2 ppm of methanol and <50 ppm of hydrocarbons.

EXAMPLE 10

Example 10 was out according to example 9. The feed to the dimethylether column consisted of 5979 kg/h of methanol, 79 kg/h of water and 203 kg/h of dimethylether. The mixture was fed to the column at the 45th tray. The reflux ratio was 1:15. Distillate (21 kg/h with 10 kg of DME) containing contaminations was withdrawn at the 50th tray. 193 kg/h of pure DME were withdrawn at the 33rd tray. 1 kg/h of inerts were withdrawn at the head. 6047 kg of bottoms were fed into the methanol column and separated into 5978 kg of methanol and 79 kg of water. The DME thus obtained, was odorless and contained 3 ppm of methanol and <50 ppm of hydrocarbons.

In the following examples 11-13 different feed-blends were used. The time of operation was 48 hours in each run.

EXAMPLE 11

Example 11 was carried out according to example 9. The reaction product consisted of 188 kg of unreacted methanol, 1708 kg of water and 4365 kg of dimethylether. The mixture was fed to the distillation column at the 28th tray. The reflux ratio was 1:0,4. At the 22nd tray 91 kg/h (with 90 kg of DME) of distillate containing contaminations was withdrawn. At the 17th tray 4275 kg of pure DME were withdrawn. At the head of the column 4 kg/h of inerts were obtained. 1895 kg/h of bottoms were fed into the methanol column and separated into 187 kg/h of methanol and 1708 kg/h of water. Methanol was recycled to the dimethylether synthesis reactor. The DME thus obtained had a weak odor.

COMPARATIVE EXAMPLE 11a

Example 11 was repeated, however the pH in the bottom of the DME-column was adjusted to 7,5-8,5 with 10% NaOH aqueous solution. DME thus obtained was odorless. An analogous result was obtained with LiOH and Mg(OH)$_2$ as a base.

EXAMPLE 12

A 7185 kg/h dehydration mixture from a DME-synthesis reactor, was fed into a DME-distillation column equipped with 65 bubble trays. The mixture consisted of 4300 kg of DME, 1200 kg of methanol and 1685 kg of water. Feed tray was the 51st tray. At the 7th tray 4220 kg of DME were withdrawn. At the 40th tray 82 kg/h (with 80 kg of DME) of a distillate containing contaminations were withdrawn. 1198 kg of methanol and 1685 of water were fed into the methanol column. Methanol was distilled off and recycled to the synthesis reactor. DME thus obtained had a weak odor.

COMPARATIVE EXAMPLE 12a

Example 12 was repeated but the pH in the bottom of the dimethylether column was adjusted to 12 (with aqueous 12% NaOH solution). The DME thus obtained was odorless.

EXAMPLE 13

3000 kg/h of a feed product consisting of 2940 kg of dimethylether, 30 kg of methanol and 30 kg of water were fed to a column equipped with 10 valve trays. The mixture was fed to the column one tray above the bottom. 1465 kg/h of distillate containing contaminations and consisting essentially of DME were withdrawn at the 5th tray (technical quality). 1475 kg/h pure, odorless DME were withdrawn at the 9th tray (from the bottom) containing 1 ppm of methanol and <50 ppm of hydrocarbons.

Examples 1 and 2 show that by addition of methanol as a washing liquid the quantity of pure DME can be increased.

Examples 3 and 3a show that also in the case of addition of crude methanol as a washing liquid an increased quantity of pure DME can be obtained.

Example 4 discloses a typical integrated distillation of crude methanol from a methanol synthesis unit and dehydration product from a dimethylether synthesis unit.

The ratio of the two products is 11:1, it may however, as outlined above, depending on the capacity of the units, strongly vary.

Example 4 shows that highly pure DME can be obtained at the mode of operation described, without impairing the production of pure methanol (not disclosed in this example).

Example 5 shows, that also water and methanol/water mixture lead to improved DME-quality.

Examples 6, 6a and 6b show that even in the case of deviation from the inventive distillation process, the use of washing liquid leads to an increased quality of DME.

Examples 7 and 8 demonstrate that in the case of applying a very low reflux ratio based on the DME-concentration in the feed and withdrawal of contaminations and pure DME in the borderline area with regard to the trays for withdrawal for these products, an odor detected in DME can be removed by addition of a base or base mixtures and adjustment of pH >7 in the bottom.

Examples 9 and 10 show that at a distance of at least 8 trays from feed tray to tray of withdrawal of DME an odorless DME can be obtained.

Examples 11 and 12 show that by recycling of methanol distilled off in the methanol column to the DME synthesis reactor a weak odor may appear in the DME-distillate, which can however be removed by the inventive adjustment of the pH in the bottom of the DME-distillation column.

Example 13 shows that even in a very short distillation column pure odorless DME can be obtained according to the invention.

The instant invention demonstrates that in principle in all cases of inventive distillation in particular at modes of operation in borderline cases with regard to the scope of the invention, adjustment of the pH is of great importance for obtaining a pure odorless DME.

We claim:

1. Process for the purification of dimethylether comprising:
    a. catalytically dehydrating methanol at a temperature of 140°–500° C. and a pressure of 1–50 bars by distillation of the dehydration product, wherein the dehydration product is fed in gaseous or liquid state into a distillation column having a plurality of trays at one or more feed trays with the lowest feed tray being the first tray above the bottom of the distillation column;
    b. withdrawing at least one liquid or gaseous fraction, containing contaminants at one or more trays, wherein the tray is at least 3 trays below the lowest tray from which distilled dimethylether is withdrawn to at least 5 trays above the bottom of the distillation column;
    c. withdrawing distilled dimethylether at one or more trays wherein the lowest tray from the head of the column is
        i) in the case of one feed tray at least 8 trays above the feed tray or
        ii) in the case of several feed trays, when the quantity of dehydration product which is fed to the highest feed tray is greater than 0 to less than 100% of the total feed, the lowest tray from which distilled dimethylether is withdrawn is at least 1 to at least 8 trays above the highest feed tray whereby the distance between the highest feed tray and the lowest tray from which distilled dimethylether is withdrawn increase with increasing quantity of feed fed to the highest feed tray, and
    d. adjusting the pH of the dehydration product in the bottom of the dimethylether column to at least 7.

2. Process according to claim 1, wherein for the adjustment of the pH NaOH or KOH is used.

3. Process according to claim 1, wherein in addition to the dehydration product from a dimethylether synthesis reactor, a washing liquid is added.

4. Process according to claim 3 wherein the washing liquid is methanol or a mixture of methanol and water.

5. Process according to claim 3, wherein the washing liquid is water.

6. Process according to claim 3, wherein light components, which are withdrawn from the head of the distillation column for the production of dimethylether, which contain $CO_2$, $N_2$, light hydrocarbons and dimethylether, are washed in order to recover dimethylether, by countercurrent, cross or parallel flow washing, with methanol as washing liquid.

7. Process according to claim 3, wherein the washing liquid is fed into the distillation column below the tray from which the fraction containing the contaminations is withdrawn.

8. Process according to claim 3 wherein the dehydration product contains up to 5 weight % of dimethylether and the reflux ratio is from 1:0.2 to 1:100.

9. Process according to claim 8 wherein the reflux ratio is from 1:0.2 to 1:25.

10. Process according to claim 3 wherein the dehydration product contains from greater than 5 weight % to less than 20 weight % of dimethylether and the reflux ratio is from 1:0.2 to 1:50.

11. Process according to claim 10 wherein the reflux ratio is from 1:0.2 to 1.25.

12. Process according to claim 3 wherein the dehydration product contains from 20 to 80 weight % of dimethylether and the reflux ratio is from 1:0.2 to 1:50.

13. Process according to claim 12 wherein the reflux ratio is from 1:1 to 1:5.

14. Process according to claim 3 wherein the dehydration product contains from 80 to 100 weight % of dimethylether and the reflux ratio is from 1:0.2 to 1:10.

15. Process according to claim 14 wherein the reflux ratio is from 1:0.2 to 1:5.

* * * * *